(12) United States Patent
Shi et al.

(10) Patent No.: US 8,181,921 B2
(45) Date of Patent: May 22, 2012

(54) PLATFORM TELESCOPING MECHANISM

(75) Inventors: Zhiyuan Shi, Shenzhen (CN); Xiaohong Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 552 days.

(21) Appl. No.: 12/365,832

(22) Filed: Feb. 4, 2009

(65) Prior Publication Data
US 2009/0236487 A1    Sep. 24, 2009

(30) Foreign Application Priority Data
Mar. 24, 2008 (CN) .......................... 2008 1 0066173

(51) Int. Cl.
*F16M 11/00* (2006.01)
*E04G 1/00* (2006.01)

(52) U.S. Cl. ............... 248/125.8; 248/125.2; 182/2.2; 182/2.11; 182/141; 212/348

(58) Field of Classification Search ........... 248/125.2, 248/125.8, 157, 419, 420, 422, 424, 298, 248/125.1, 370; 182/2.1, 2.2, 2.11, 2.7, 2.9, 182/19, 141, 148; 212/278, 347, 348, 349, 212/350; 414/541, 540, 543, 556, 921; 187/200
See application file for complete search history.

(56) References Cited

U.S. PATENT DOCUMENTS

| | | | | |
|---|---|---|---|---|
| 4,160,492 A * | 7/1979 | Johnston | ........................ | 182/2.2 |
| 4,456,093 A * | 6/1984 | Finley et al. | .................... | 182/2.2 |
| 4,775,288 A * | 10/1988 | Dimitriu | ...................... | 414/708 |
| 5,163,570 A * | 11/1992 | Mundis et al. | ................ | 212/278 |
| 5,249,642 A * | 10/1993 | Kishi | ............................. | 182/2.11 |
| 5,995,893 A * | 11/1999 | Lee et al. | ......................... | 701/50 |
| 6,405,114 B1 * | 6/2002 | Priestley et al. | ................ | 701/50 |
| 7,798,760 B2 * | 9/2010 | Strassman et al. | ............ | 414/462 |

FOREIGN PATENT DOCUMENTS

| CN | 2188216 Y | 1/1995 |
|---|---|---|
| CN | 1137747 A | 12/1996 |
| CN | 1153848 A | 7/1997 |
| CN | 2511666 Y | 9/2002 |
| CN | 2537740 Y | 2/2003 |
| CN | 2732841 Y | 10/2005 |

(Continued)

OTHER PUBLICATIONS

Search Report for Chinese Application No. 200810066861.4 dated Jun. 12, 2008.

(Continued)

*Primary Examiner* — Tan Le
(74) *Attorney, Agent, or Firm* — Vista IP Law Group, LLP

(57) ABSTRACT

Disclosed are various embodiments of a platform telescoping system which comprises a platform, a first supporting arm, a second supporting arm, a telescopic driving mechanism which comprises a first power output, end and a rotational driving mechanism which comprises a second power output end. The first power output end is integrated with the second supporting arm and causes the second supporting arm to move in a first direction, and the second power output end is integrated with the platform and causes the platform to pivot between a first position and a second position. The second supporting arm telescopes with respect to the first supporting arm for adjusting the position of the platform. The space occupied by the platform telescoping system may be reduced while its functions enhanced.

16 Claims, 5 Drawing Sheets

FOREIGN PATENT DOCUMENTS

| | | |
|---|---|---|
| CN | 1724198 A | 1/2006 |
| CN | 2780550 Y | 5/2006 |
| CN | 2790116 Y | 6/2006 |
| CN | 1819755 A | 8/2006 |
| CN | 1822759 A | 8/2006 |
| CN | 2853914 Y | 1/2007 |
| JP | 2002093964 A | 3/2002 |
| JP | 2003017879 A | 1/2003 |
| JP | 2004158629 A | 6/2004 |

OTHER PUBLICATIONS

"Shielding: Suffering from Heat Exhaustion" Laird Technologies.
"Design of Heat Dissipation and Electromagnetic Shielding of High Power Amplifier Array" Xie Tianyu. 2002. vol. 18. No. 4.
English Translation of Abstract for CN 2790116.
English Translation of Abstract for CN 1819755.
English Translation of Abstract for CN 1822759.
English Translation of Abstract for JP 2002093964.
English Translation of Abstract for JP 2003017879.
English Translation of Abstract for JP 2004158629.
English Translation of Abstract for "Design of Heat Dissipation and Electronagmetic Shielding of High Power Amplifier Array".
English Translation of Abstract for "Shielding: Suffering from Heat Exhaustion".
Search Report for Chinese Application No. 200810066173.8 dated Jun. 12, 2008.
"Basis and Application of a Grab with Hydraulic Rotating Elements".
"Design and Error Analysis of a Fork Leveling Mechanism of a Telescopic Handler".
English Translation of Abstract for CN2780550.
English Translation of Abstract for CN1153848.
English Translation of Abstract for CN2853914.
English Translation of Abstract for CN1137747.
English Translation of Abstract for CN2188216.
English Translation of Abstract for CN1724198.
English Translation of Abstract for CN2732841.
English Translation of Abstract for CN2537740.
English Translation of Abstract for "Basis and Application of a Grab with Hydraulic Rotating Elements".
English Translation of Abstract for "Design and Error Analysis of a Fork Leveling Mechanism of a Telescopic Handler".

\* cited by examiner

PLATFORM TELESCOPING MECHANISM

CROSS-REFERENCE TO RELATED APPLICATION

This application claims the benefit of Chinese Patent Application No. 200810066173.8 which is filed on Mar. 24, 2008 into State Intellectual Property Office of the People's Republic of China.

FIELD OF INVENTION

The present invention relates to a platform telescoping mechanism.

BACKGROUND ART

A cantilevered X-ray digital camera system generally comprises a platform which is mounted on a carriage. The carriage may be attached to an upright column by using a supporting arm or other structural members. The platform may be driven by or move along with the carriage along the upright column to move up and down. Meanwhile, the platform may be able to rotate around the supporting arm by a certain angle. X-ray photographing of various target locations on patients may be benefited by the capability of the platform to move up and down and to rotate about one or more certain axes.

The supporting arm in these x-ray imaging systems generally has a fixed length. With the systems where the supporting arm is longer, the platform is thus extended farther away from the upright column and offers better flexibility in the positioning the patients for imaging. Thus, it may be easier to find a better imaging position with respect to the patient with a longer supporting arm. However, longer supporting arms inevitably occupy larger space and often causes difficulty for hospital staff to manipulate the imaging instrument and/or adjust or fine tune the patient's position for better imaging. Longer supporting arms may also cause hospital personnel and the imaging instrument or other medical equipment to compete for the limited space. On the other hand, where the supporting arm is shorter, the platform is situated closer to the upright column so the overall footprint of the imaging system may be reduced. Nonetheless, after the hospital bed is placed onto the platform, adjustment is generally needed to get better imaging results. This is especially true when considering that the target locations on different patients, even for the same diagnostic purpose, are generally different such that fine adjustment may be necessary and may often be difficult for an imaging system with a short supporting arm.

SUMMARY OF INVENTION

An object of various embodiments of the invention is to overcome the disadvantages found in the prior art by providing a platform telescoping apparatus which occupies a smaller foot print than similar conventional systems and offers at least two degree of freedom to adjust the position of the platform.

In some embodiments, a platform telescoping system comprises a platform, a first supporting arm, a second supporting arm, a linear driving mechanism which comprises a first power output end, and a rotational driving mechanism which comprises a second power output end, wherein the platform and the second supporting arm may be pivotally connected to each other directly or indirectly at a pivot joint, the first supporting arm and the second supporting arm may be connected to each other in a way to allow linear movement with respect to each other, the telescopic driving mechanism may be attached to the first supporting arm, the first power output end may be coupled to the second supporting arm and drives the second supporting arm to move substantially horizontally in a first direction, the rotational driving mechanism is attached to the second supporting arm, and the second power output end is coupled with the platform and drives the platform to pivot between a first position and a second position. In some embodiments, the first position comprises a substantially upright position, and the second position comprises a substantially horizontal position. One of ordinary skill in the art would clearly know and understand that the first position comprises a substantially upright position, and that the second position comprises a substantially horizontal position due to manufacturing tolerances, clearance or allowance as designed, and/or combination thereof even though the first position and the second position may be intended to or designed to be in the perfectly upright position and perfectly horizontal position.

In some embodiments, the platform comprises a base and a pedestal. The pedestal comprises a first end attached or connected to or otherwise integrated with the base and a second end connected or connected to or otherwise integrated with the second power output end. In some embodiments, the second end connected or connected to or otherwise integrated with the second power output end by using a hinge to allow certain range of relative motion in at least one degree of freedom between the second end and the second power output end.

In some embodiments, the second supporting arm comprises a support body which is connected or attached to or otherwise integrated with the second supporting arm. In some embodiments, the second supporting arm is connected or attached to or otherwise integrated with the rotational driving mechanism by using a hinge to allow certain range of relative motion in at least one degree of freedom between the second supporting art and the rotational driving mechanism.

In some embodiments, the rotational driving mechanism comprises an electrically or pneumatically driven linear motion mechanism.

In some embodiments, the telescopic driving mechanism comprises a driving source which causes a rotational movement and a motion transforming mechanism for transforming the rotational movement into a linear translational movement, and the first power output end is attached or connected to or otherwise integrated with the motion transforming mechanism. In some embodiments, the motion transforming mechanism comprises a rack and pinion mechanism or ball screws to transform rotational movement into linear translational movement. In some embodiments, the motion transforming mechanism comprises a friction drive which relies on intersurface friction rather than positive engagement as in the case of a rack and pinion mechanism.

In some embodiments, the driving source comprises a motor and a speed reducer coupled thereto. In some embodiments, the speed reducer comprises a worm drive which serves to reduce rotational speed or to allow higher torque to be transferred. In some embodiments, the motion transforming mechanism comprises a gear and pinion mechanism which further comprises a gear which is attached to an output shaft of the speed reducer and a gear rack arranged in the first direction and attached or connected to the second supporting arm.

In some embodiments, the speed reducer comprises a worm drive. In these embodiments, the output shaft of the speed reducer, the worm gear, and the gear are coaxially connected together.

In some embodiments, a first linear track is attached to one of the first supporting arm and the second supporting arm in the first direction. In these embodiments, a track mounting seat is attached to the other of the first supporting arm and the second supporting arm, and the first linear track is engaged with the track mounting seat in a way to allow sliding motion with respect to each other.

In some embodiments, a second linear track is attached or connected to either the first supporting arm or the second supporting arm in the first direction, a clearance adjusting mechanism is attached to the other of the first supporting arm and the second supporting arm. In some embodiments, the clearance adjusting mechanism comprises a first mounting shaft, a first adjustment wheel, a second mounting shaft, and a second adjustment wheel, wherein the first mounting shaft and the second mounting shaft may both be attached to a corresponding one of the supporting arms in a substantially horizontal orientation, the first adjustment wheel is eccentrically attached to the first mounting shaft, the second adjustment wheel is attached to the second mounting shaft, and the second linear track is situated between the first adjustment wheel and the second adjustment wheel.

In some embodiments, the first supporting arm is attached to the second supporting arm with a elastic member. In some embodiments, the elastic member comprises a spring. In some embodiments, the elastic member extends or compresses in the longitudinal direction during certain movement of the second supporting arm. In some embodiments, the elastic member comprises a first end connected to the first supporting arm and a second end connected to the second supporting arm.

In some embodiments, the first supporting arm and the second supporting arm are both of cylindrical shapes along the first direction. In some embodiments, the first supporting arm encases or encloses the second supporting arm. In some embodiments, the rear end of the second supporting arm protrudes out from the first supporting arm, and the platform is pivotally connected to the rear end of the second supporting arm by using a pivotable joint.

In some embodiments, a retention stop is attached or connected to or otherwise integrated with the first supporting arm for restraining or limiting movement or range of motion of the horizontal movement of the second supporting arm.

In various embodiments, the second supporting arm is able to telescoping in a first direction with respect to the first supporting arm. In some embodiments after the patient's position has been adjusted by hospital personnel, the second supporting arm may then extend or retract substantially along the direction of the first supporting or the second supporting arm. After imaging, the platform, in some embodiments, retracts in a substantially horizontal direction so as to save or conserve the space occupied by the imaging system. For example, when a patient is about to receive chest x-ray, the platform may be configured to be in an upright position, and the first supporting arm may be configured to be in a retracted position.

BRIEF DESCRIPTION OF THE DRAWINGS

The drawings illustrate the design and utility of various embodiments of the invention, in which similar elements are referred to by common reference numerals. In order to better appreciate how advantages and objects of various embodiments of the inventions are obtained, a more particular description of various embodiments of the inventions briefly described above will be rendered by reference to specific embodiments thereof, which are illustrated in the accompanying drawings. Understanding that these drawings depict only typical embodiments of the invention and are not therefore to be considered limiting its scope, the invention will be described and explained with additional specificity and detail through the use of the accompanying drawings.

DETAILED DESCRIPTION OF THE PREFERRED EMBODIMENTS

Figure 1:
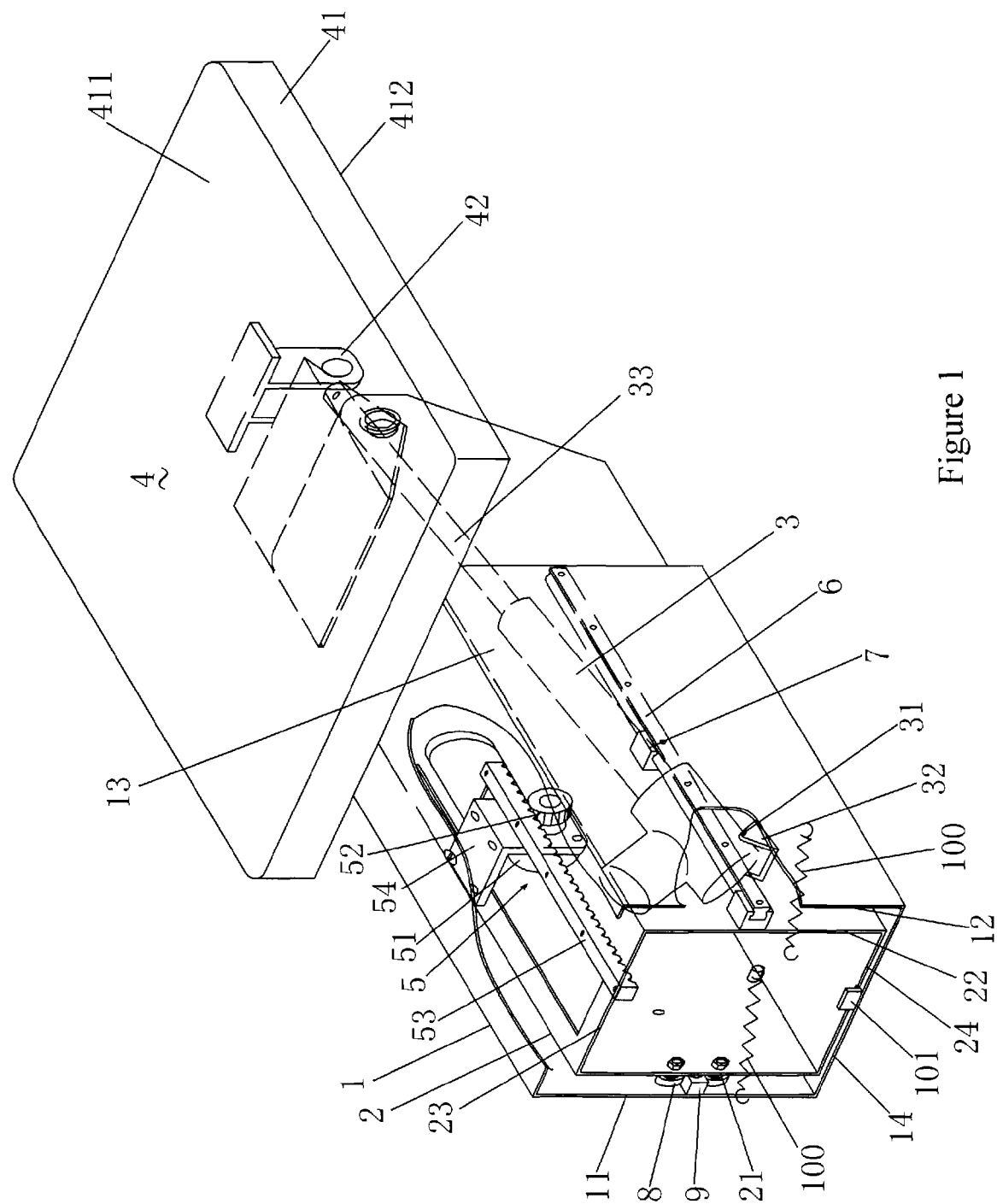
FIG. 1 illustrates a structural schematic view of a platform telescoping mechanism according to an embodiment.

As shown in FIGS. 1 to 7, a platform telescoping mechanism according to various embodiments comprises a platform 4, a first supporting arm 1, a second supporting arm 2, a telescopic driving mechanism 5 comprising a first power output end, and a rotational driving mechanism 3 comprising a second power output end. The platform 4 and the second supporting arm 2 are rotatably or pivotally connected or attached to or otherwise integrated with each other by using a respective rotational or pivotable joint, and the first supporting arm 1 and the second supporting arm 2 are coupled with each other along a linear direction by using a translational joint. In some embodiments, the telescopic driving mechanism 5 may be attached or connected to or otherwise integrated with the first supporting arm 1 and comprises a first power output end which is connected to the second supporting arm 2 and drives the second supporting arm 2 to move in a first direction. In some embodiments, the rotational driving mechanism 3 is attached or connected to or otherwise integrated with the second supporting arm 2 and comprises a second power output end which is connected to the platform 4 and drives the platform 4 to rotate about a first axis between a first position and a second position. In some embodiments, the first position comprises a substantially upright position. In some embodiments, the second position comprises a substantially horizontal position. One of ordinary skill in the art would clearly know and understand that the first position comprises a substantially upright position, and that the second position comprises a substantially horizontal position due to manufacturing tolerances, clearance or allowance as designed, and/or combination thereof even though the first position and the second position may be intended to or designed to be in the perfectly upright position and perfectly horizontal position.

In some embodiments, the first supporting arm 1 comprises a hollow generalized cylinder extending in a first direction. In some embodiments, the hollow generalized cylinder comprises a rectangular, square, or circular cross section. One of ordinary skills in the art would clearly understand and appreciate that the first and the second support arms may also comprise various other cross-sectional shapes. In some embodiments where the hollow generalized cylinder comprises a rectangular or a square cross section, the first supporting arm 1 comprises a first left outer wall 11, a first right outer wall 12, a first top outer wall 13, and a first bottom outer wall 14, all of which extend in the first direction; the first left outer wall 11 and the first right outer wall 12 are both orientated in a substantially vertical direction; and the first top outer wall 13 and the first bottom outer wall 14 are both orientated in a substantially horizontal direction; the first top and bottom outer walls 13, 14 are connected to the upper and lower ends of the first left and right outer walls 11, 12 respectively. The second supporting arm 2 comprises a second left inner wall 21, a second right inner wall 22, a second top inner wall 23, and a second bottom inner wall 24, all of which extend in the first direction in some embodiments. The second left inner wall 21 and the second right inner wall 22 may both be orientated in a substantially vertical direction, and the second top inner wall 23 and the second bottom inner wall 24 may both be orientated in a substantially horizontal direction in some embodiments. The second top and bottom inner walls 23, 24 may be connected to the upper and lower ends of the second left and right inner walls 21, 22 in some embodiments. The first direction comprises a direction as shown in the direction of the arrowheads labeled "A" in FIG. 2.

In some embodiments, the first supporting arm 1 encases or includes the second supporting arm 2 so that the second supporting arm 2 is at least partly encased or included within the first supporting arm 1. In some embodiments, the rear end 25 of the second supporting arm 2 protrudes horizontally out from the first supporting arm 1. The rotational driving mechanism 3 comprises a linear electric or pneumatic drive situated in the second supporting arm 2 and pivotably or rotatably mounted to a support body 32 by using a pivot pin 31. The support body 32 may be fixedly attached to the inside of the second supporting arm 2 so that the linear electric or pneumatic drive may be pivot around an axis of the pivot pin 31 inside the second supporting arm 2 within a certain range of angle in some embodiments. The platform 4 comprises a base 41 and a pedestal 42 in some embodiments. The base 41 defines an upper surface 411 and a lower surface 412, both of which are parallel with each other. A hospital bed may be placed onto the upper surface 411 of the base 41 in some embodiments. The pedestal 42 may extend is a substantially perpendicular direction from the base 41 and comprises a first end fixedly or removably attached to the lower surface 412 of the base 41 and a second end connected to a push rod 33 of the linear electric or pneumatic drive by using a hinge 43 in some embodiments. The push rod 33 extends at least partly out of the second supporting arm 2 in some embodiments. The lower surface 412 of the base 41 may be pivotably or rotatably mounted to the rear end 25 of the second supporting arm 2 by using a connecting pin 44 in some embodiments. In some embodiments when the electric pusher is activated, the push rod 33 of the linear electric or pneumatic drive causes the pedestal 42 to move, and the pedestal 42 in turn causes the base 41 to pivot around an axis of the connecting pin 44 so that the linear motion of the push rod 33 may be transformed into the circular motion of the platform 4 in some embodiments. In some embodiments, the pivoting direction of the platform is illustrated as the direction as shown with arrow "B" in FIG. 2. In some embodiments, the push rod 33 forms the second power output end of the rotational driving mechanism 3.

In various embodiments, the telescopic driving mechanism 5 comprises a driving source 51, a gear 52, and a gear rack 53. The driving source 51 may be fixedly or removably attached or connected to or otherwise integrated with the first top outer wall 13 of the first supporting arm 1 by using one or more L-shaped connecting plates 54. The second top inner wall 23 of the second supporting arm 2 may be formed with a slot 231 through which the connecting plate 54 extends, so that the telescopic driving mechanism 5 may be disposed in the second supporting arm 2 in its entirety. The gear 52 my be fixedly or rotatably attached or connected to or otherwise integrated with an output shaft 511 of the driving source 51 in some embodiments. The gear rack 53, which engages the gear 52, is oriented in the first direction and is fixedly or removably attached or connected to or otherwise integrated with the second top inner wall 23 of the second supporting arm 2. In some embodiments when the driving source 51 is activated, its output shaft 511 causes the gear 52 to rotate or spin, the gear 52 in turn causes the gear rack 53 to move linearly, and the gear rack 53 causes the second supporting arm 2 to move linearly in the first horizontal direction in some embodiments. The driving source 51 comprises an electrical motor and a speed reducer 512 in some embodiments. In some embodiments, the speed reducer comprises a worm drive. The motor shaft of the motor may be coupled with the worm of the worm drive to transmit torque and may be substantially aligned with the worm in some embodiments. The gear 52 and the worm gear of the worm drive may both be fixedly or removably connected or attached to the output shaft 511 of the driving source 51 in some embodiments. In some embodiments, the output shaft 511, the gear 52, and the worm gear may be coaxially aligned. In some embodiments, the gear rack 53 forms the first power output end of the telescopic driving mechanism 5.

For supporting the second supporting arm 2 and guiding its linear movement in some embodiments, at least one track mounting seat 7 is attached to the second right inner wall 22 of the second supporting arm 2 in some embodiments. When several track mounting seats 7 are provided, all the track mounting seats 7 are located on the same level in some embodiments. A first linear track 6, which is disposed in the first direction, is attached to the first right outer wall 12 of the first supporting arm 1. The first linear track 6 is mounted in the track mounting seat 7 and is integrated with the track mounting seat 7 to allow relative sliding motion between the first linear track and the track mounting seat in some embodiments. A clearance adjustment mechanism 8 is attached to the second left inner wall 21 of the second supporting arm 2 in some embodiments. The clearance adjustment mechanism 8 comprises a first mounting shaft 81, a first adjusting wheel 82, a second mounting shaft 83, and a second adjusting wheel 84 in some embodiments. The first mounting shaft 81 and the second mounting shaft 83 may both be orientated in a substantially horizontal direction with the first mounting shaft 81 being directly above the second mounting shaft 83 in some embodiments. The first adjustment wheel 82 may be coaxially attached to the first mounting shaft 81, and the second adjustment wheel 84 may be coaxially attached to the second mounting shaft 83 in some embodiments. The first and second mounting shafts 81, 83 are both attached to the second left inner wall 21 of the second supporting arm 2 by nuts 85 or other fasteners in some embodiments. A second linear track 9, which may be oriented in the first direction, may be attached to the first left inner wall 11 of the first supporting arm 1 in some embodiments. The second linear track 9 may be mounted between the first adjustment wheel 82 and the second adjustment wheel 84 in some embodiments. By rotating the second mounting shaft 83, the second adjustment wheel 84 may rotate eccentrically around an axis of the second mounting shaft 83 so that the distance or gap between the first adjustment wheel 82 and the second adjustment wheel 84 may be adjusted or fine tuned in some embodiments.

In some embodiments, the first left outer wall 11 of the first supporting arm 1 and the second left inner wall 21 of the second supporting arm 2 may be coupled with each other by using an elastic member 100. In these embodiments where the second supporting arm 2 moves and thus the elastic member 100 extends and compresses substantially linearly for performing the telescoping function. In some embodiments where first or the second supporting arm comprises a rectangular or square cross section hollow generalized cylinder, the elastic member 100 is attached to the first or the second supporting arm such that the elastic member 100 is sitting at an angle with respect to the first bottom outer wall 14 of the first supporting arm 1. In some embodiments where the elastic member 100 comprises a tension spring, as the outward moving distance of the second supporting arm 2 with respect to the first supporting arm 1 becomes larger, the angle between the elastic member 100 and the first bottom outer wall 14 decreases while the elastic member 100 extends longer to produce larger compression force, which results in decreasing or eliminating the clearance between the first supporting arm 1 and the second supporting arm 2. In some embodiments where the elastic member 100 comprises a compression spring, as the second supporting arm 2 extends, telescopes, or protrudes further out of the first supporting arm 1, the elastic member 100 compresses and becomes shorter to produce larger tension force. In some embodiments, the platform telescoping system may further comprise an additional elastic member may be provided for attaching the first right outer wall 12 or another part of the first supporting arm 1 to the second right inner wall 22 or another part of the second supporting arm 2 so that the two elastic members may be disposed in a substantially symmetric manner. One of ordinary skills in the art would know that the elastic member(s) 100 may comprise other types of spring(s) than tension and compression springs. In some embodiments, a retention stop 101 may be attached or connected to or otherwise integrated with the first bottom outer wall 14 or other part(s) of the first supporting arm 1 for restraining the retraction motion of the second supporting arm 2. In some embodiments, another retention stop may also be attached or connected to or otherwise integrated with the first bottom outer wall 14 of the first supporting arm 1 for restraining the extension motion of the second supporting arm 2.

In some embodiments during assembly, the first supporting arm 1 may be attached or connected to or otherwise integrated with the upright column 102 or may be attached or connected to or otherwise integrated with a carriage attached to the upright column 102. In some embodiments where the platform telescoping system comprises the carriage, the entire platform may move up and down along the upright column.

The following paragraphs describe more details of the operation of the platform telescoping system in some embodiments.

Figure 2:
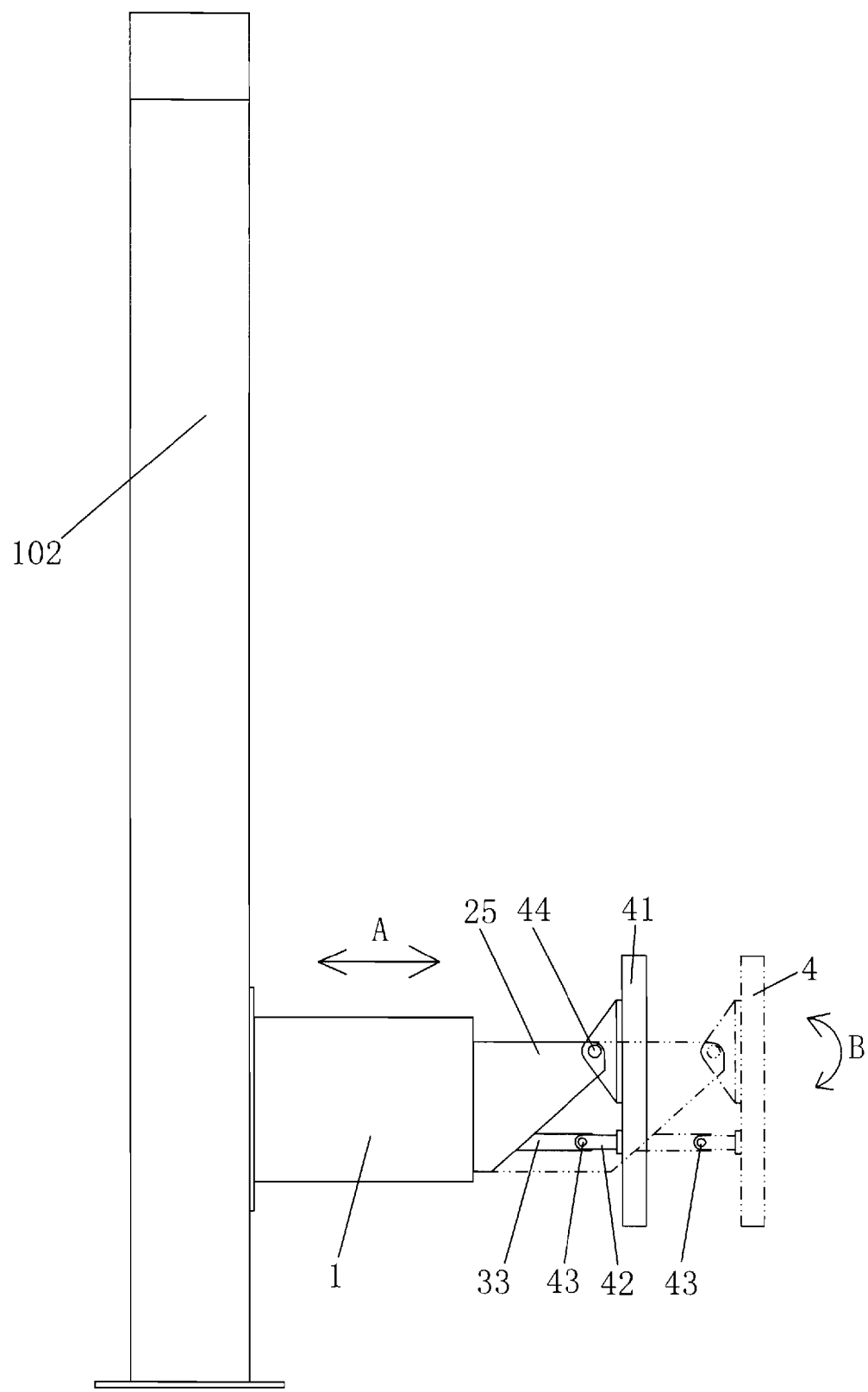
FIG. 2 illustrates a schematic view of the platform according the embodiment of the present invention in a substantially vertical position.
Figure 3:
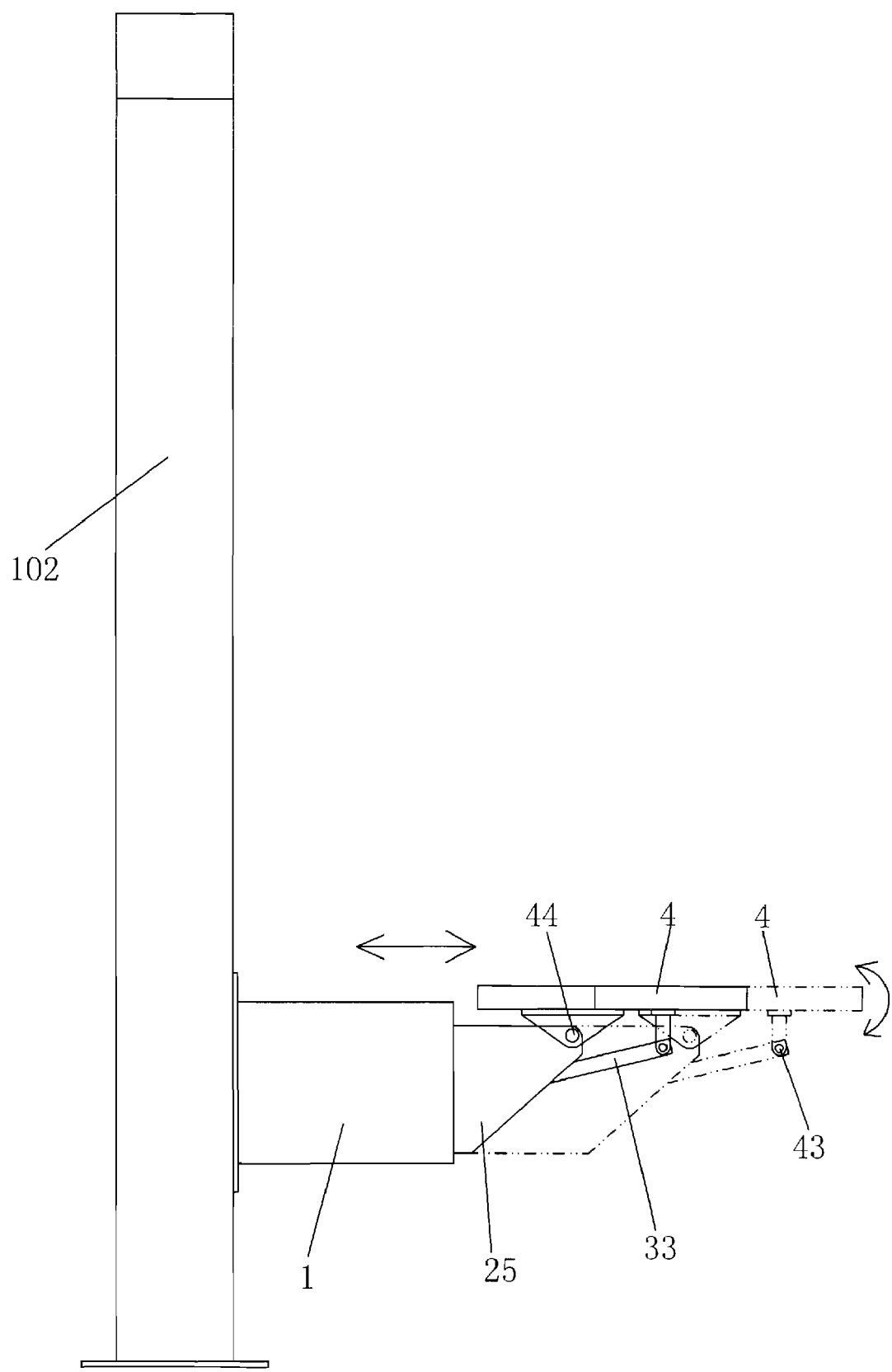
FIG. 3 illustrates a schematic view of the platform according the embodiment of the present invention in a substantially horizontal position.
Figure 4:
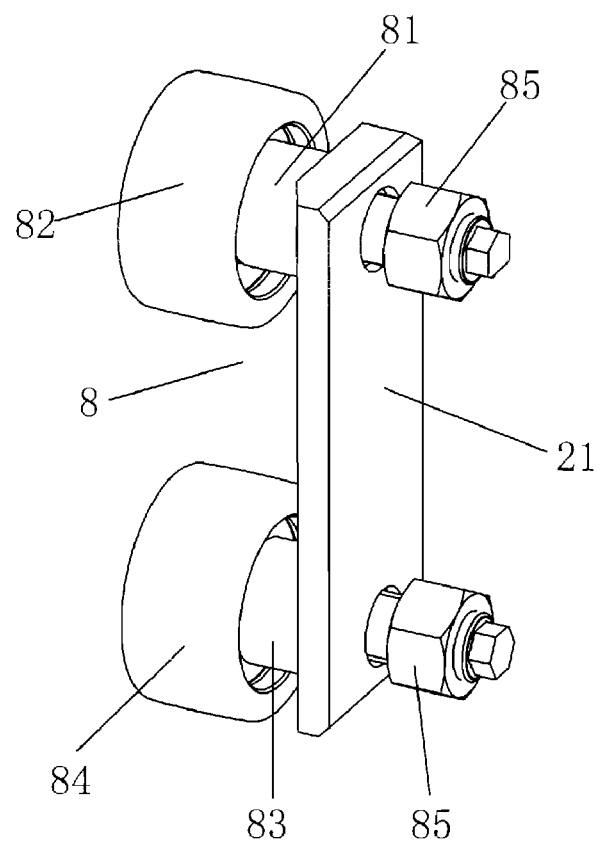
FIG. 4 illustrates a structural schematic view of a clearance adjustment mechanism according to an embodiment.
Figure 5:
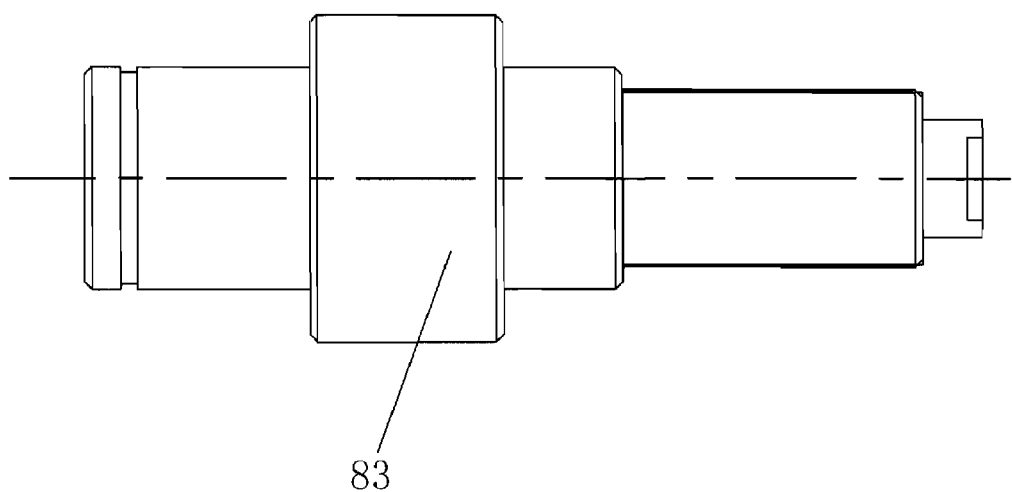
FIG. 5 illustrates a front view of a second mounting shaft according to an embodiment.
Figure 6:
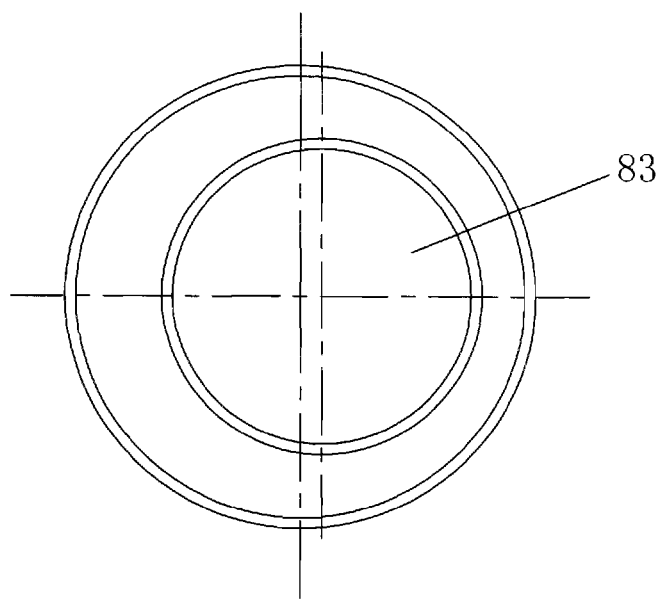
FIG. 6 illustrates a right side view of a second mounting shaft according to an embodiment.
Figure 7:
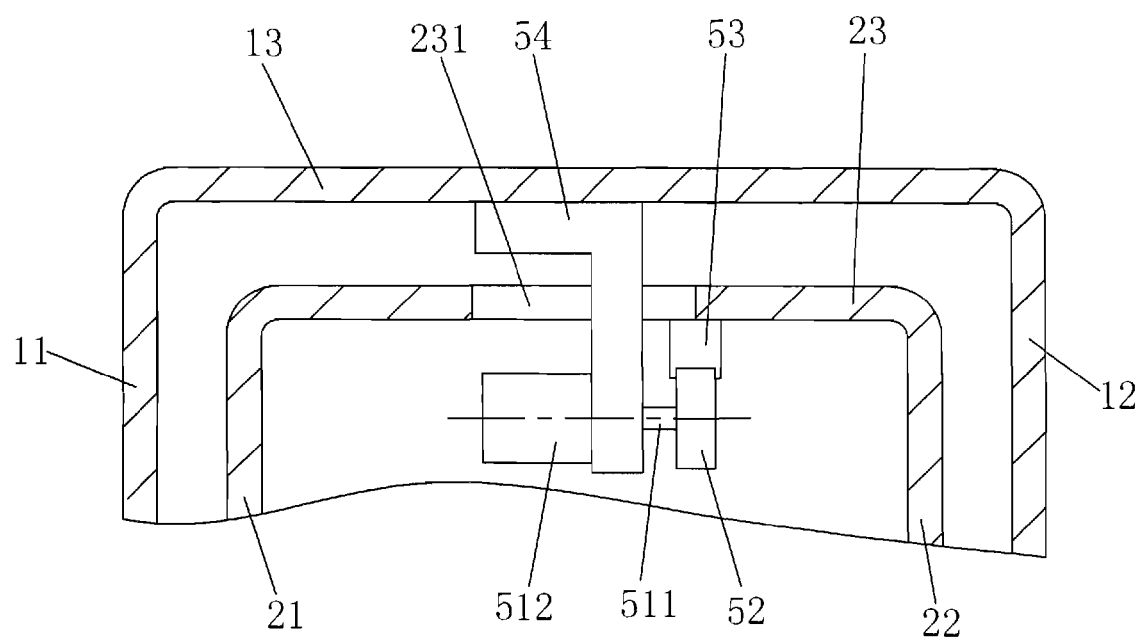
FIG. 7 illustrates a schematic view showing a telescopic driving mechanism, a first supporting arm, and a second supporting arm according to an embodiment.

As shown in FIG. 2, in the initial position, the platform 4 is situated in a substantially vertical orientation in some embodiments. FIG. 2 illustrates a state of the platform telescoping system where the platform 4 is situated in a vertical orientation, and the second supporting arm 2 extends to the limit extension position as shown in dotted lines in FIG. 2. In some embodiments where the speed reducer 512 causes the gear 52 to rotate, the gear 52 in turn causes the gear rack 53 to move linearly. As a result, in these embodiments, the second supporting arm 2 linearly extends or retracts in the first direction under the guide of the first linear track 6 and the second linear track 9. In some embodiments where it may be required to turn or swing the platform 4 around a certain axis, the linear electric or pneumatic drive drives the platform 4 so that the platform 4 turns or pivots around an axis of the connecting pin 44. FIG. 3 illustrates a state of the platform telescoping system where the platform 4 is situated in a horizontal orientation and the second supporting arm 2 extends to the limit extension position as shown in dotted lines in some embodiments.

In some embodiments, the rotational driving mechanism 3 causes the platform 4 to turn or pivot around a pivot axis in some embodiments. In some embodiments, the rotational driving mechanism 3 may comprise a bar linkage mechanism or other mechanisms that may cause the platform 4 to turn or pivot around an axis.

In some embodiments, the telescopic driving mechanism 5 causes the second supporting arm 2 to move substantially linearly with respect to the first supporting arm 1 in the first direction. In some embodiments, the telescopic driving mechanism comprises a driving source and a rack and pinion mechanism or other mechanisms for similar purposes for transforming the output rotational movement or motion of the driving source into a linear movement or motion. In some embodiments, the rack and pinion mechanism or other mechanisms for similar purposes may be substituted by any other mechanisms that may transform a rotational movement or motion into a linear movement, such as a screw-nut mechanism or two components that form a kinetic pair and may move with respect to each other with one or more constraints controlling the relative motion or positions of the two components. In some embodiments, the telescopic driving mechanism 5 may also comprises a driving source which produces or causes linear movement or motion. In these embodiments, such a driving source may comprise a speed reducer.

In some embodiments, the first linear track 6 and the second linear track 9 are configured to provide or perform a precise guiding function as well as to reinforce the strength of the whole platform telescoping system. In some embodiments, the platform telescoping system comprises zero, one, or more than two linear tracks. In some embodiments, the linear track may be mounted to either the first supporting arm 1 or the second supporting arm 2. In some embodiments, the linear tracks may be mounted either to the left and right sides of the supporting arm or to the upper and lower sides of the supporting arm, so that the linear tracks causes the second supporting arm 2 to extend and retract in the first direction.

In some embodiments, the platform telescoping system may comprise the clearance adjustment mechanism 8 for adjusting the clearance or allowance between the adjustment wheel(s) and the linear track(s). In some embodiments, the platform telescoping system may comprise no clearance adjustment mechanism. In some embodiments, there may be only one adjustment wheel which is eccentrically mounted or aligned with respect to the corresponding mounting shaft. In some embodiments, the two adjustment wheels are both eccentrically mounted or aligned with respect to their corresponding mounting shafts.

In some embodiments, the initial position of the platform 4 comprises a substantially vertical position, where the platform 4 is situated outside the rear end 25 of the second supporting arm 2. In some embodiments, the position of the platform 4 during imaging comprises a substantially horizontal position, where the platform 4 is substantially parallel to the second supporting arm 2 and may be situated slightly higher than the rear end 25 of the second supporting arm 2. In some embodiments, the mounting position of the platform 4 on the rear end 25 of the second supporting arm 2 may be suitably determined so that the platform 4 does not interfere with the first supporting arm 1 and the second supporting arm 2 when the platform 4 is turning or pivoting. In some embodiments, the initial position of the platform may be another upright position where the platform is situated at a certain angle with respect to the vertical direction.

In some embodiments for the platform telescoping system, the sequence of motion of the pivoting of the platform and the telescopic motion of the platform may be determined according to requirement. In some embodiments, the platform may first pivot or rotate around an axis and then telescopically move in a first linear direction, or first telescopically move in a first linear direction and then pivot or turn around an axis, or telescopically move in a first linear direction and pivot around an axis simultaneously.

In some embodiments for the platform telescoping system, the platform telescoping system may be used in cantilevered X-ray digital imaging systems, and the platform telescoping system may also be used in other medical and/or surgical equipment where the platform telescoping system provides positional adjustments in some embodiments. In some embodiments, the platform telescoping system may further provide the capabilities or functionalities to detect relevant parts of the equipment such as the operation table(s) or carrier platform(s).

Other aspects and features of the invention will be evident from reading the following detailed description of the preferred embodiments, which are intended to illustrate, not limit, the invention. Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed is:

1. A platform telescoping system, comprising:
    a platform; and
    a second supporting arm at least part of which is encased within a first supporting arm, wherein the platform is pivotally attached to the second supporting arm to pivot around a first axis, which is substantially parallel to a weight bearing surface of the platform, to a position that reduces a footprint of the platform telescoping system, and the first supporting arm encases at least the part of the second supporting arm to allow the second supporting arm to telescope in a first direction and to pivot around a first axis by using a telescopic driving mechanism and a rotational driving mechanism;
    a first linear track and a second linear track which is attached to at least one of the first supporting arm and the second supporting arm in the first direction;
    a track mounting seat which is attached to one of the first supporting arm and the second supporting arm that is not attached to the first linear track, wherein the first linear track and the track mounting seat move along a second direction with respect to each other;
    a clearance adjusting mechanism which is attached to one of the first supporting arm and the second supporting arm that is not attached to the second linear track, wherein the clearance adjusting mechanism comprises a first mounting shaft, a first adjustment wheel attached to the first mounting shaft; and
    a second adjustment wheel eccentrically attached to a second mounting shaft, wherein the first mounting shaft and the second mounting shaft are attached to their respective supporting arms, and the second linear track is situated between the first adjusting wheel and the second adjusting wheel.

2. The platform telescoping system of claim 1, wherein the platform comprises a base and a pedestal, and the pedestal comprises a first end attached to the base and a second end attached to a second power output end by a hinge.

3. The platform telescoping system of claim 2, wherein the second supporting arm comprises a support body which is attached to the second supporting arm and is attached to the rotational driving mechanism.

4. The platform telescoping system of claim 3, wherein the rotational driving mechanism comprises a linear electric or pneumatic driving mechanism.

5. The platform telescoping system of claim 1, wherein the telescopic driving mechanism comprises:
    a driving source which outputs a rotational movement and a motion transforming mechanism for transforming the rotational movement into a linear movement, and
    a first power output end which is attached to the motion transforming mechanism.

6. The platform telescoping system of claim 5, wherein the driving source comprises a motor coupled to a speed reducer, and the motion transforming mechanism comprises a rack and pinion mechanism which comprises:
    a gear coaxially attached to an output shaft of the speed reducer; and
    a gear rack arranged in the first direction and attached to the second supporting arm.

7. The platform telescoping system of claim 6, wherein the speed reducer comprises a worm drive.

8. The platform telescoping system of claim 1, the system further comprises:
    an elastic member which is attached to the first supporting arm and the second supporting arm to contribute to a telescoping motion of the second supporting arm.

9. The platform telescoping system of claim 1, wherein the first supporting arm comprises a hollow generalized cylinder to encase the second supporting arm.

10. The platform telescoping system of claim 1, the system further comprises:
    a retention stop which is integrated with the first supporting arm for restraining movement of the second supporting arm.

11. The platform telescoping system of claim 1, the platform further comprising:
    the weight bearing surface to support a subject on the platform.

12. The platform telescoping system of claim 11, wherein the platform is actuated between at least a first position and a second position.

13. The platform telescoping system of claim 12, wherein the platform is actuated to the first position in which the weight bearing surface is maintained in a substantially horizontal orientation to support the objet on the platform.

14. The platform telescoping system of claim 12, wherein the platform is actuated to the first position in which at least one of the first supporting arm and the second supporting arm is maintained in the substantially horizontal orientation to support the subject on the platform.

15. The platform telescoping system of claim 12, wherein the platform is actuated to the second position in which the weight bearing surface is maintained in a substantially vertical orientation to reduce the footprint of the platform telescoping system.

16. A platform telescoping system, comprising:
a platform;
a second supporting arm at least part of which is encased within a first supporting arm, wherein
the platform is pivotally attached to the second supporting arm to pivot around a first axis, and
the first supporting arm encases at least the part of the second supporting arm to allow the second supporting arm to telescope in a first direction and to pivot around a first axis by using a telescopic driving mechanism and a rotational driving mechanism;
a first linear track which is attached to at least one of the first supporting arm and the second supporting arm in the first direction;
a track mounting seat which is attached to one of the first supporting arm and the second supporting arm that is not attached to the first linear track, wherein
the first linear track and the track mounting seat move along a second direction with respect to each other;
a second linear track which is attached to one of the first supporting arm and the second supporting arm in the first direction;
a clearance adjusting mechanism which is attached to one of the first supporting arm and the second supporting arm that is not attached to the second linear track, wherein the clearance adjusting mechanism comprises a first mounting shaft, a first adjustment wheel attached to the first mounting shaft; and
a second adjustment wheel eccentrically attached to a second mounting shaft, wherein
the first mounting shaft and the second mounting shaft are attached to their respective supporting arms, and
the second linear track is situated between the first adjusting wheel and the second adjusting wheel.

* * * * *